United States Patent
Shin et al.

(10) Patent No.: US 10,016,471 B2
(45) Date of Patent: Jul. 10, 2018

(54) SOLID PHARMACEUTICAL COMPOSITIONS OF BROWN ALGAE

(71) Applicant: PHLORONOL, INC., San Francisco, CA (US)

(72) Inventors: Hyeon-Cheol Shin, Bonney Lake, WA (US); Hyejeong Hwang, Bonney Lake, WA (US)

(73) Assignee: Phloronol, Inc., San Francisco, CA (US)

( * ) Notice: Subject to any disclaimer, the term of this patent is extended or adjusted under 35 U.S.C. 154(b) by 0 days.

(21) Appl. No.: 15/194,470

(22) Filed: Jun. 27, 2016

(65) Prior Publication Data

US 2016/0375070 A1 Dec. 29, 2016

Related U.S. Application Data

(60) Provisional application No. 62/186,354, filed on Jun. 29, 2015.

(51) Int. Cl.
| | | |
|---|---|---|
| *A61K 36/03* | (2006.01) | |
| *A61K 9/20* | (2006.01) | |
| *A61K 9/00* | (2006.01) | |
| *A61J 3/10* | (2006.01) | |
| *A61J 3/00* | (2006.01) | |

(52) U.S. Cl.
CPC .............. *A61K 36/03* (2013.01); *A61J 3/10* (2013.01); *A61K 9/0056* (2013.01); *A61K 9/2054* (2013.01); *A61K 9/2077* (2013.01); *A61J 3/005* (2013.01)

(58) Field of Classification Search
CPC .. A61J 3/005; A61J 3/10; A61K 36/03; A61K 9/0056; A61K 9/2054; A61K 9/2077
See application file for complete search history.

(56) References Cited

U.S. PATENT DOCUMENTS

| | | |
|---|---|---|
| 5,427,798 A | 6/1995 | Ludwig et al. |
| 8,518,446 B2 | 8/2013 | Ashraf et al. |
| 2006/0246128 A1 | 11/2006 | Nagi et al. |
| 2010/0247586 A1 | 9/2010 | Hugerth et al. |
| 2011/0111027 A1 | 5/2011 | Rourke et al. |
| 2014/0235705 A1* | 8/2014 | Cardoso ............... A61K 9/0019 514/447 |

OTHER PUBLICATIONS

McHugh, "A Guide to the Seaweed Industry", 2003, Food and Agricultural Organization of the United Nations, FAO Fisheries Technical Paper No. 441.*
McHugh, "A Guide to the Seaweed Industry", No. 441, 2003, p. 39, retrieved from ftp://ftp.fao.org/docrep/fao/006/y4765e/y4765e00.pdf on Aug. 29, 2016.
Singh et al., Phloroglucinol Compounds of Natural Origin, Nat Prod Rep 23:558-591 (2006).

* cited by examiner

*Primary Examiner* — Michael B. Pallay
(74) *Attorney, Agent, or Firm* — Young Basile Hanlon & MacFarlane, P.C.

(57) ABSTRACT

Described herein are solid pharmaceutical compositions of brown algae extracts and methods for making solid pharmaceutical compositions of brown algae extracts. In some embodiments, the brown algae extract is derived from *Ecklonia cava*.

22 Claims, 1 Drawing Sheet

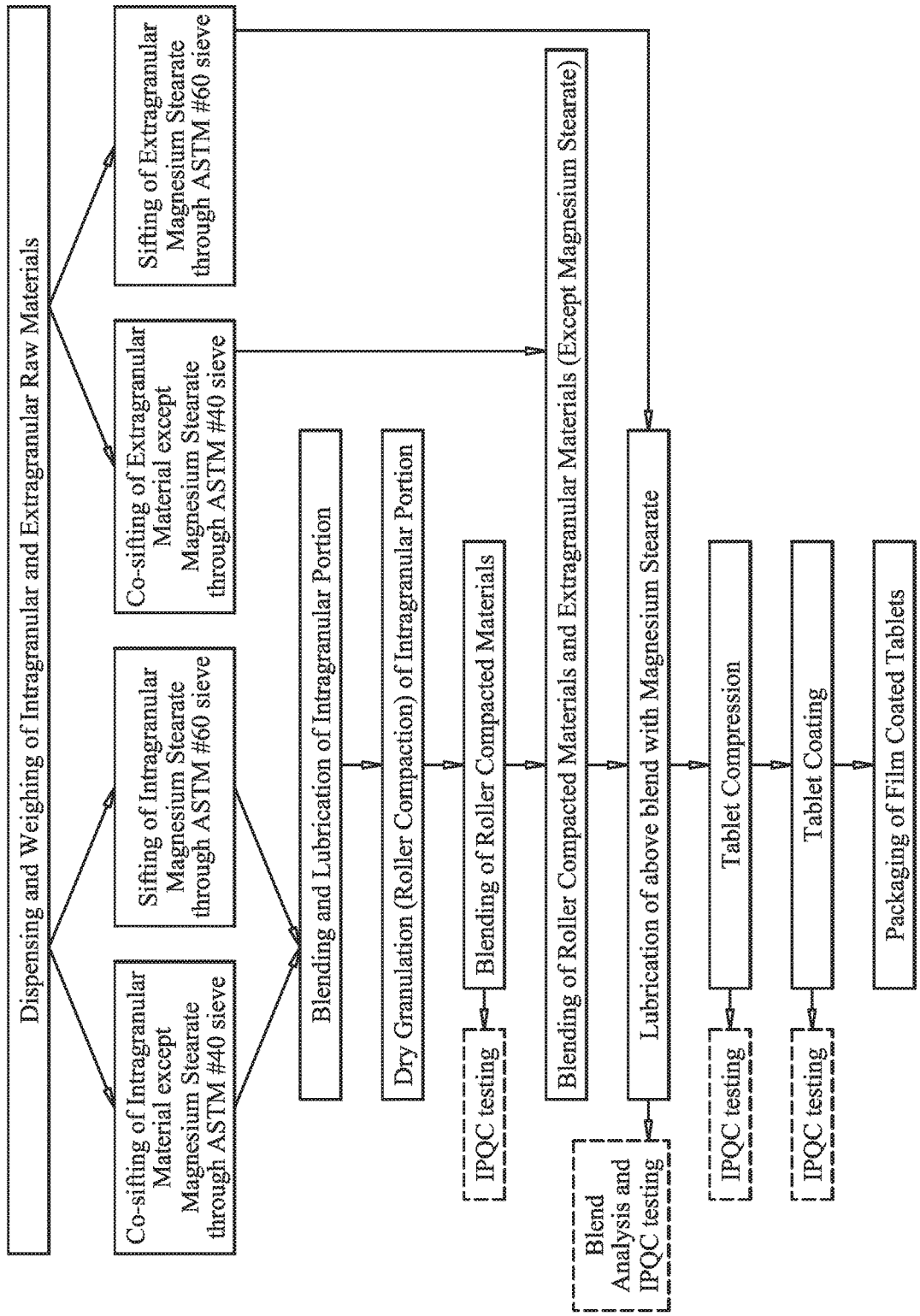

SOLID PHARMACEUTICAL COMPOSITIONS OF BROWN ALGAE

CROSS-REFERENCE TO RELATED APPLICATION

This application claims priority under 35 U.S.C. § 119 (e) from U.S. Provisional Application Ser. No. 62/186,354, filed Jun. 29, 2015, which is hereby incorporated by reference in its entirety.

FIELD

Described herein are solid pharmaceutical compositions of brown algae extracts and methods for making solid pharmaceutical compositions of brown algae extracts. In some embodiments, the brown algae extract is derived from *Ecklonia cava*.

BACKGROUND

Brown algae, belong to the Laminariaceae family and are found in abundance in central and southern Japan and Korea. Though mostly used as sources for alginic acid, these algae are also widely consumed as food in many Asian and several European countries. Brown algae have two major chemical groups: polysaccharides and polyphenols. Polysaccharide components include alginates, laminarin and fucoidans. Brown algal polyphenols are specifically called phlorotannins. Among categories of phlorotannins, eckol derivatives are pharmacologically prominent. These polyphenolic compounds are characterized by a dibenzo-1,4-dioxin unit in the molecular skeleton which is found only in some specific brown algae such as *Eisenia* and *Ecklonia* species.

Medicinally active brown algae extracts are typically alcohol extracts of the dehydrated leaves of the brown seaweed of the Laminariaceae family. An example is a purified *Ecklonia cava* extract standardized to contain approximately 92% phlorotannins and known by the brand name SEAPOLYNOL (also known as PH100). This formulation of *Ecklonia cava* extract has been approved as a New Dietary Ingredient (NDI) for use by adults and children over the age of 12 and is currently being consumed by humans in dietary supplements marketed in the US, Korea, China and Japan.

A variety of physical or physicochemical characteristics of the active substance are relevant for the preparation of solid oral dosage forms, (e.g., oral powders, granules, pellets, tablets, capsules, chewable tablets, dispersible tables, troches or lozenges), such as, for example, correct assay, content and mass uniformity, chemical and physical stability of the drug product, proper dissolution rate, physical characteristics of the drug substance such as, for example, bulk densities (i.e., poured and tapped density) Hausner Factor, particle morphology, shape, the ratio of length to width for needles, size distribution, electrostatic charging and surface adhesive properties.

Brown algae extracts have a variety of challenging physiochemical properties relevant for preparation of a solid oral dosage form. Depending on the method of preparation, formulations of the extract can be highly hygroscopic, poorly disintegrated or with poor flow properties which leads to tablets with insufficient hardness, poor coating, poor disintegration properties or poor productivity. Accordingly what is needed are solid dosage forms which satisfactorily addresses the above problems.

SUMMARY

The present invention satisfies these and other needs by providing in one aspect a solid pharmaceutical composition of an extract of brown algae which is stable to moisture, has sufficient hardness and acceptable disintegration properties. The solid pharmaceutical composition of brown algae includes an intragranular portion which encompasses an extract of brown algae, disintegrant, filler and binder, an extragranular part comprising disintegrant, filler, lubricant and binder and a coating.

In another aspect, a method of preparing a stable rapidly disintegrating oral dosage form of an extract of brown algae is provided. The method includes blending an extract of brown algae with one or more intragranular excipients, granulating the blend to form granules, blending the granules with one or more extragranular excipients, compressing the blend into a tablet and coating the tablet.

BRIEF DESCRIPTION OF THE FIGURES

The FIGURE illustrates the process flow for formulation development of PH100 tablets.

DETAILED DESCRIPTION

In a first aspect, a solid pharmaceutical composition of an extract of brown algae is provided. The solid pharmaceutical composition of brown algae includes an intragranular portion which encompasses an extract of brown algae, disintegrant, filler and binder, an extragranular part which encompasses disintegrant, filler, lubricant and binder and a coating. In some embodiments, the extract of brown algae is a dried extract.

In some embodiments, the composition is an immediate release composition. In other embodiments, the composition disintegrates in about 30 minutes or less. In still other embodiments, the composition disintegrates in about 20 minutes or less. In still other embodiments, the composition disintegrates in about 15 minutes or less. In still other embodiments, the composition disintegrates in about 10 minutes or less. In still other embodiments, the composition disintegrates in about 5 minutes or less. In still other embodiments, the composition disintegrates in about 3 minutes or less.

In some embodiments, the composition is formed into a tablet. In other embodiments, the tablet has a friability of less than about 1%, less than about 0.8%, less than about 0.5% or less than about 0.3%. In still other embodiments, the tablet has a hardness of between about 8 and about 25 Kp.

In some embodiments, the intragranular portion and extragranular portion are present in a ratio (w:w) of between about 3:1 and about 1:1. In other embodiments, the intragranular portion and extragranular portion are present in a ratio (w:w) of between about 2.15:1 and about 1.95:1.

In some embodiments, the intragranular portion comprises between about 30% to about 70% dried extract, between about 20% to about 60% filler, between about 0.5% to about 5% binder and between about 4% to about 11% disintegrant. In some embodiments, the intragranular part further includes a lubricant and glidant.

In some embodiments, the intragranular portion is between about 30% to about 70% extract, between about 20% to about 60% filler, between about 0.5% to about 5% binder, between about 0.4% to about 1.2% lubricant, between about 0.4% to about 1.2% glidant and between about 6% to about 9% disintegrant. In other embodiments, the intragranular portion is between about 40% to about 60% dried extract, between about 30% to about 50% filler, between about 0.75% to about 2.5% binder, between about 0.6% to about 1.2% lubricant, between about 0.6% to about 1.2% glidant and between about 4% to about 11% disintegrant. In still other embodiments, the intragranular portion is compressed to form granules.

In some embodiments, the extragranular portion is between about 70% and about 95% filler and between about 5% and about 30% disintegrant. In other embodiments, the extragranular portion includes a lubricant and a glidant. In still other embodiments, the extragranular portion is between about 70% and about 95% filler, between about 5% and about 30% disintegrant, between about 0.5% and about 4% lubricant and between about 0.5% and about 4% glidant. In still other embodiments, the extragranular portion is between about 80% and about 90% filler, between about 7% and about 14% disintegrant, between about 1% and about 2% lubricant and between about 1% and about 2% glidant.

In some of the above embodiments, the solid pharmaceutical composition includes a coating. In other embodiments, the coating is film coating.

In some of the above embodiments, the intragranular portion of the solid pharmaceutical composition includes PH100, microcrystalline cellulose, lactose monohydrate, croscarmellose sodium, hydroxypropyl methylcellulose, colloidal silicon dioxide and magnesium stearate. In other of the above embodiments, the extragranular portion of the solid pharmaceutical composition includes avicel, croscarmellose sodium, colloidal silicon dioxide and magnesium stearate. In still other of the above embodiments, the intragranular portion of the solid pharmaceutical composition includes PH100, microcrystalline cellulose, lactose monohydrate, croscarmellose sodium, hydroxypropyl methylcellulose, colloidal silicon dioxide and magnesium stearate and the extragranular portion of the solid pharmaceutical composition includes avicel, croscarmellose sodium, colloidal silicon dioxide and magnesium stearate.

In many of the above embodiments, the tablet is film-coated with opaque lavender. In some embodiments, the opaque lavender is Opadry Purple YS-1-4845.

In some embodiments, a method of preparing a stable rapidly disintegrating oral dosage form of an extract of brown algae is provided. The method includes blending an extract of brown algae with one or more intragranular excipients, granulating the blend to form granules, blending the granules with one or more extragranular excipients, compressing the blend into a tablet and coating the tablet. In other embodiments, granulating the blend to form granules includes roller compressing the blend to form granules. In still other embodiments, the tablet is film-coated with opaque lavender. In still other embodiments, the opaque lavender is Opadry Purple YS-1-4845.

In many of the above embodiments, the brown algae extract is derived from *Ecklonia cava, Ecklonia kurome, Ecklonia stolonifera, Ecklonia maxima, Ecklonia radiata, Eisenia bicyclis, Eisenia arborea* or combinations thereof. In some embodiments, the brown algae extract contains more than about 20% pholorotannins. In other embodiments, the brown algae extract contains more than about 90% pholorotannins. In still other embodiments, the brown algae extract is derived from *Ecklonia cava*.

Phlorotannins are a subset of polyphenols found primarily in brown seaweed. Phlorotannins are the only polyphenols found in brown seaweeds and can be quantitated using the Folin-Ciocalteu's Methanol Method. In terms of chemical structure, phlorotannins are oligomers and polymers based on the monomer phloroglucinol which is a 1,3,5,-trihydroxybenzene. These monomers are joined by either ether (phlorethols), phenyl (fucols), ether and phenyl (fucophlorethols), or dibenzodioxin (eckols) linkages (Singh et al., Phloroglucinol Compounds of Natural Origin, *Nat Prod Rep* 23:558-591 (2006)). Some of the phlorotannins can be separated by reverse-phase HPLC and some cannot. The structures of some major phlorotannins are provided below.

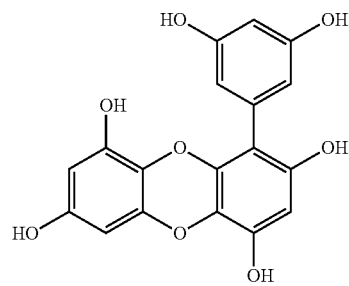

Eckol

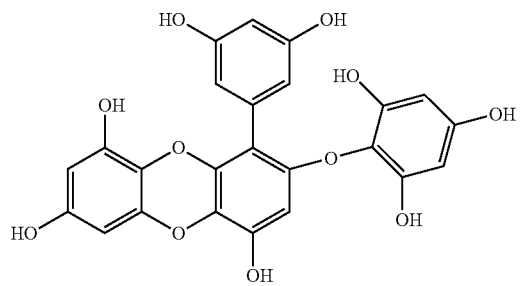

2-Phloroeckol

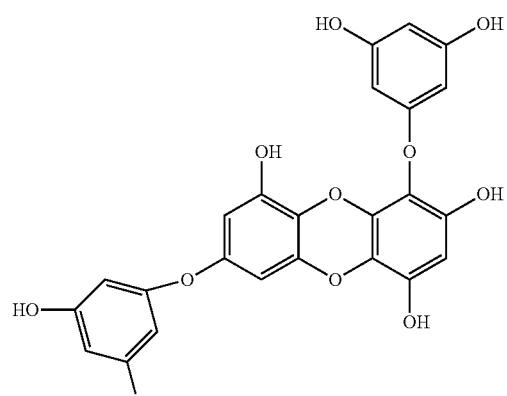
7-Phloroeckol
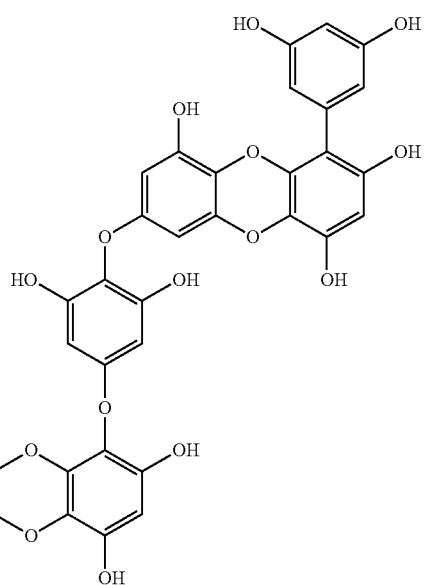
Dieckol
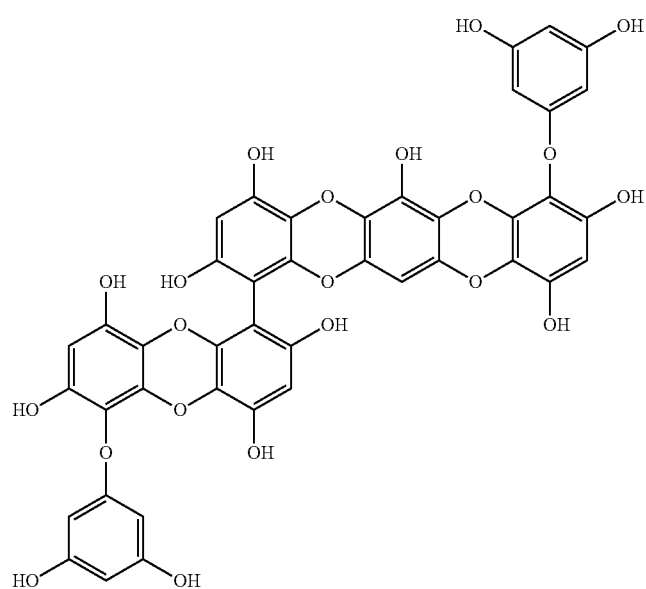
6,6'-Bieckol
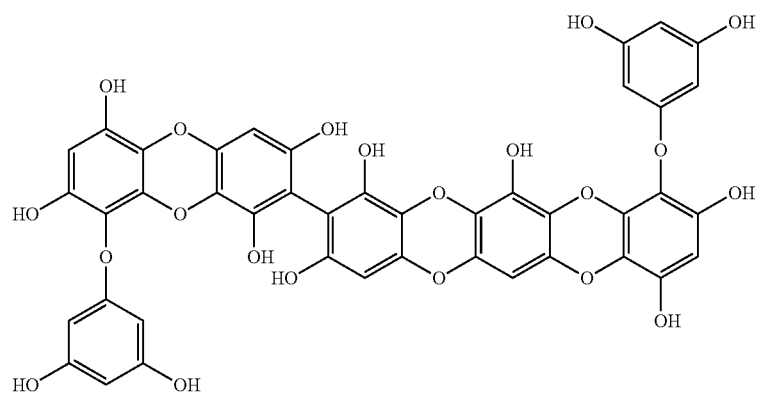
8,8'-Bieckol

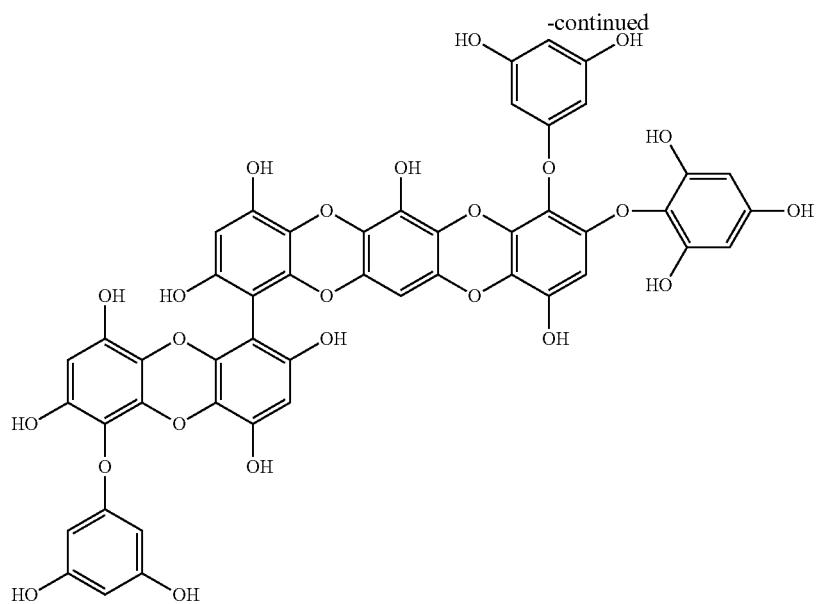

2-O-(2,4,6-trihydroxyphenyl)-6,6'-Bieckol

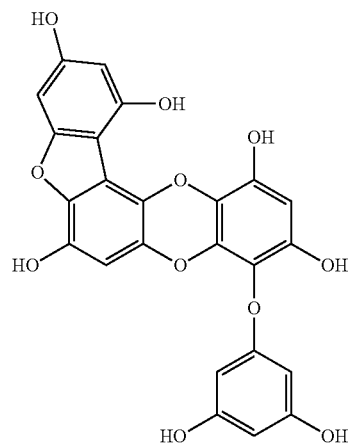

Fucofuroeckol A

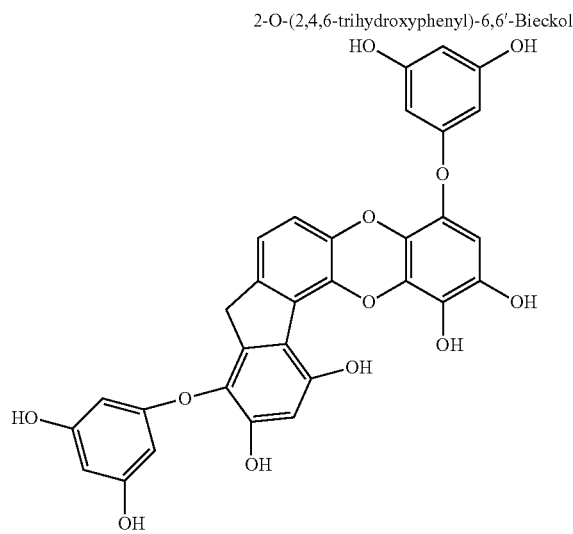

Pholorofucofuroeckol A

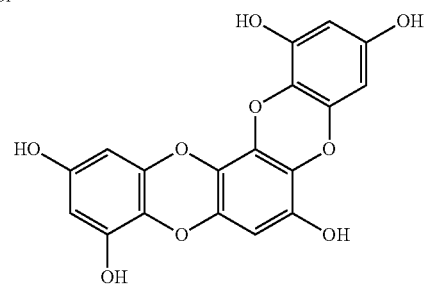

Dioxinodehydroeckol

In some embodiments, the *Ecklonia cava* extract comprises about 92 wt % pholorotannins and is known as PH100. PH100 API is manufactured by Botamedi Inc., Jeju, Korea. PH100 is a dark brown powder and is composed of approximately 92% phlorotannins among which 30-40% can be identified on a weight basis. The most abundant phlorotannins present in PH100 are dieckol and bieckols. Dieckol is approximately 14-24% by area of the HPLC-detectable phlorotannins in the PH100 mixture and approximately 8% by weight. The cluster of bieckols which includes 6, 6'-bieckol, 2-O-(2,4,6-trihydroxyphenyl)-6, 6'-bieckol, and 8, 8'-bieckol composes approximately 30% of the HPLC-detectable peaks of the PH100 API. Additional components of the botanical PH100 currently thought to have pharmacologic activity include phlorofucofuroeckol A (PFF-A) which represents 3-9% by area percent of PH100.

In addition to the phlorotannins in PH100 that can be separated by HPLC, a number of minor structures characterized by a continuum of molecular weights and polarity that cannot be separated are also present. These inseparable and thus unidentified structures are considered likely to be open-chain polymers of phloroglucinol joined by linkages such as ether (phlorethols), phenyl (fucols), ether and phenyl (fucophlorethols) with various regiochemistries and varying degrees of polymerization.

The oral dosage forms described herein, especially tablets, may also contain fillers. Fillers generally refer to substances which form the body of the tablet in the case of tablets with small amounts of active agent (e.g., less than 60% by weight). Accordingly, fillers dilute the active agents in order to produce an adequate tablet-compression mixture. The normal purpose of fillers, therefore, is to obtain a suitable tablet size. In many of the above embodiments, the fillers have an average particle size (D50) of between about 30 and about 160 μm, of between about 50 and about 150 μm and of between about 70 and about 130 μm. Examples of fillers include, but are not limited to, lactose, lactose derivatives, starch, starch derivatives, treated starch, chitin, cellulose and derivatives thereof, calcium phosphate, sucrose, calcium carbonate, magnesium carbonate, magnesium oxide, maltodextrin, calcium sulfate, dextrates, dextrin and/or dextrose, hydrogenated vegetable oil, sugar alcohols and/or disaccharides, such as mannitol, sorbitol, xylitol, isomalt, glucose, fructose, maltose and mixtures thereof. The term "sugar alcohols" in this context also includes monosaccharides.

Binders hold the ingredients in a tablet together and ensure that tablets and granules can be formed with required mechanical strength and give volume to tablets. Examples of binders include, but are not limited to, saccharides and their derivatives (e.g., disaccharides, sucrose, lactose, etc.) polysaccharides and their derivatives (e.g., starches, cellulose or modified cellulose, etc.) such as microcrystalline cellulose and cellulose ethers such as hydroxypropyl cellulose (HPC), sugar alcohols such as xylitol, sorbitol or maltitol, gelatin, synthetic polymers (e.g., polyvinylpyrrolidone (PVP), polyethylene glycol (PEG), etc.) or combinations thereof.

Disintegrants are substances or mixture of substances added to a tablet to facilitate its breakup or disintegration after administration. Examples of disintegrants include starches, clays, celluloses (e.g., low substituted hydroxypropyl cellulose, alginates, gums, cross-linked polymers, etc.). In some embodiments, the disintegrant is a super disintegrant. Super disintegrants include, but are not limited to, croscarmellose, cross linked poly vinyl pyrollidine, crospovidone, sodium starch glycolate, hydroxypropyl cellulose LH-11, hydroxypropyl cellulose LH-21 or combinations thereof.

In some embodiments, the disintegrant and other excipients are split into two portions. One portion is added to the API and binder prior to granulation. The second portion is mixed with the granulated API prior to making a tablet. Incorporated in this manner, the disintegrant serves a double purpose. The portion added just prior to tableting, upon administration, rapidly breaks down the tablet into granules. The disintegrant mixed with the API disintegrates the granules into smaller particles, thus maximizing the surface area for subsequent solvation of the active ingredient.

Lubricants are employed in the manufacture of certain dosage forms, and will usually be used when producing tablets. Examples of lubricants include, but are not limited to, hydrogenated vegetable oils (e.g., hydrogenated cottonseed oil) magnesium stearate, sodium stearate, calcium stearate, stearic acid, sodium lauryl sulfate, glyceryl behapate, magnesium lauryl sulfate, talc, waxes, liquid paraffin, boric acid, sodium benzoate, sodium oleate and mixtures thereof. In some embodiments, the dosage form includes one or more pharmaceutically acceptable lubricants, such as, for example, magnesium stearate. Lubricants generally comprise between about 0.2% to about 7.0% of the total tablet weight.

Glidants are substances that improve flow characteristics of a powder mixture. In some embodiments, the dosage form includes one or more pharmaceutically acceptable glidants, such as, for example, colloidal silicon dioxide, starch, hydrated sodium silicate, and talc. In other embodiments, colloidal silicon dioxide having a density of about 0.029 to about 0.040 g/ml is used to improve the flow characteristics of the formulation. It will be understood, other glidants having similar properties to colloidal silicon dioxide which are known or can be developed could be used, provided they are compatible with other excipients and the active ingredient in the formulation and which do not significantly affect the flowability, homogeneity and compressibility of the formulation. Glidants are typically provided in an amount of between about 0.1 to about 1 percent by weight of the formulation on a solid basis.

Examples of coating agents used to coat film-coated tablets include, but are not limited to a combination of substrates such as hypromellose, hydroxypropylcellulose, polyvinylpyrrolidone, hypromellose 2910, polyvinyl alcohol etc. and a plasticizer such as polyethylene glycol, propylene glycol, triacetine, triethyl citrate, glycerol, glycerin fatty acid ester, etc. In addition, additives such as titanium oxide, mannitol and the like may be added as necessary. The coating may also serve to mask taste, in the event that the extract has an unpleasant taste, which may lower patient compliance. Additionally, film coating can improve storage stability of the pharmaceutical formulation. In some embodiments, hypromellose 2910 is the substrate and polyethylene glycol is the plasticizer.

Coating agents may further contain additives usable for pharmaceutical products as long as the additive does not influence the effect of the film. Examples include, but are not limited to, light shielding agents, colorants, flavorings and the like. Addition of light shielding agents may be particularly desirable. Light shielding agents include but are not limited to, metal oxides such as titanium oxide, red ferric oxide, zinc oxide and the like, calcium salts such as calcium fluoride, calcium chloride, calcium bromide, calcium carbonate, calcium hydrogen carbonate, calcium phosphate, calcium hydrogen phosphate, calcium monohydrogen phosphate, calcium dihydrogen pyrophosphate, calcium silicate, calcium sulfate, calcium hydrogen sulfate, calcium nitrate, calcium stearate, calcium lactate and the like, magnesium salt such as magnesium hydrogen phosphate, magnesium carbonate, magnesium fluoride, magnesium silicate, magnesium stearate and the like, talc, kaolin and the like. Examples of colorants include yellow ferric oxide, red ferric oxide, riboflavins (riboflavin, riboflavin sodium phosphate), water-soluble food tar color (e.g., food color red nos. 2 and 3, food color yellow nos. 4 and 5, food color blue no. 1, etc.), water insoluble lake dye (aluminum salt of the above-mentioned water-soluble food tar color, etc.), natural dye (beta-carotene, chlorophyll, etc.) and the like. Examples of flavoring agents include sweetening agents (e.g., sucrose, invert syrup, treacle (used in chlorodyne, (i.e. chloroform and morphine tincture BPC), sorbitol, saccharine sodium, etc.), flavored syrup, ginger syrup, cocoa syrup, aromatic oils (e.g., caraway, clove, dill, lemon, orange, pepper-mint, etc.) synthetic flavors, (e.g., synthetic sweeteners, chloroform, vanillin, benzaldehyde, etc.) and variety of organic compounds like alcohols, aldehydes, esters, ketones, fatty acids and lactones are used alone or combined with essential oils.

EXAMPLES

Example 1: Preparation of Simple Tablets

Colloidal silicon dioxide and a portion of microcrystalline cellulose are mixed and passed through a 30-mesh screen. The screened material is added to a V-blender and mixed. PH100 API which has been passed through a 30-mesh screen is added and the material is remixed. Dextrin is added followed by additional mixing. The remaining microcrystalline cellulose is added and mixed. A portion of this blend is premixed with the magnesium stearate and then added back to the V-blender. The entire formulation is mixed and then sampled for in-process homogeneity testing by the QC laboratory. When the blend has passed the in-process homogeneity testing in QC, tablet pressing is then initiated.

Tablets are pressed using a standard round tablet mold and coated with 3% Lac pigment and dried. The content of each 200 mg dosage tablet is provided below in Table 1.

TABLE 1

| Ingredient | % w/w | Mg/tablet |
|---|---|---|
| PH100 | 33.3 | 200 |
| Dextrin | 16.7 | 100 |
| crystalline cellulose | 45 | 270 |
| silicon dioxide | 1 | 6 |
| magnesium stearate | 1 | 6 |
|  | 97 | 582 |
| Coating |  |  |
| HPMC | 2.07 | 12.41 |
| Titanium oxide | 0.62 | 3.73 |
| Glycerin esters of fatty acids | 0.21 | 1.24 |
| Lac pigment | 0.10 | 0.62 |
| Subtotal Coating | 3.0000 | 18.00 |
|  | 100.00% | 600.00 |

When these tablets were examined at the University of Iowa Pharmaceuticals the disintegration time was approximately 1.5 hours using the USP 2040 protocol which is not acceptable to the U.S. regulatory authorities.

Example 2: Preparation of Fast Disintegrating but Friable Tablets

In order to reduce the disintegration time, tablets were prepared using a super disintegrant (sodium starch glycolate) according to the formulation set forth in Table 2 below and a simple dry granulation and pressing as described below.

Colloidal silicon dioxide, sodium starch glycolate and a portion of microcrystalline cellulose are mixed and passed through a 30-mesh screen. The screened material is added to a V-blender and mixed. PH100 API which has been passed through a 30-mesh screen is added and mixed again. Maltodextrin is added followed by additional mixing. The remaining microcrystalline cellulose is added and mixed. A portion of this blend is premixed with the magnesium stearate and then added back to the V-blender. The entire formulation is mixed and then sampled for in-process homogeneity testing by the QC laboratory. When the blend passed the in-process homogeneity testing in QC, tablet pressing is initiated and the tablets are pressed using a 0.375"×0.625" standard oval tablet mold. Periodic samples are checked by manufacturing for tablet weight and tablet hardness throughout the process.

The tablets had acceptable disintegration time and hardness at the time of manufacture, but after 1 week when attempts were made to apply coating, the tablets were very soft and friable and broke in the coating machine.

TABLE 2

| Components, Drug Product | % w/w | Amount per tablet |
|---|---|---|
| PH 100 (API) | 34.4 | 200 mg |
| Microcrystalline Cellulose | 41.4 | 240.9 mg |

TABLE 2-continued

| Components, Drug Product | % w/w | Amount per tablet |
|---|---|---|
| Maltodextrin | 14.2 | 82.5 mg |
| Sodium Starch Glycolate | 8.0 | 46.6 mg |
| Colloidal Silicon Dioxide | 1.0 | 6 mg |
| Magnesium Stearate | 1.0 | 6 mg |
| TOTAL | 100.0 | 582 mg |

The instability of these tablets led to the following conclusions. The *Ecklonia cava* extract is hygroscopic, consequently tablets cannot be stored uncoated for periods even as short as a week. The high content of disintegrant exacerbates water uptake by the tablets. The form of the *Ecklonia cava* extract, i.e., small sticky particles, makes dry granulation unsuitable.

Example 3: Preparation of Fast Disintegrating and Sufficiently Hard Tablets

A flowchart of the manufacturing process is provided in the FIGURE and the formulation is shown in Table 3.

TABLE 3

| Ingredient | Category | % w/w | Tablet (mg) | Batch (g) |
|---|---|---|---|---|
| INTRA GRANULAR MATERIALS | | | | |
| PH100 | Active | 34.36 | 200.00 | 2400.0 |
| Microcrystalline cellulose | Filler | 19.93 | 116.00 | 1392.0 |
| Lactose monohydrate | Filler | 5.33 | 31.00 | 372.0 |
| Croscarmellose sodium | Disintegrant | 5.15 | 30.00 | 360.0 |
| Hydroxypropyl methylcellulose | Binder | 1.72 | 10.00 | 120.0 |
| Colloidal silicon dioxide | Glidant | 0.52 | 3.00 | 36.0 |
| Magnesium stearate | Lubricant | 0.52 | 3.00 | 36.0 |
| Total (Intragranular Materials) | | 67.53 | 393.00 | 4716.0 |
| EXTRA GRANULAR MATERIALS | | | | |
| Avicel PH 200-LM | Filler | 28.01 | 163.00 | 1956.0 |
| Croscarmellose sodium | Disintegrant | 3.44 | 20.00 | 240.0 |
| Colloidal Silicon dioxide | Glidant | 0.52 | 3.00 | 36.0 |
| Magnesium stearate | Lubricant | 0.52 | 3.00 | 36.0 |
| Total (Extragranular Materials) | | 32.47 | 189.00 | 2268.0 |
| Total weight (Uncoated tablet) | | 100.00 | 582.00 | 6984.0 |
| FILM COATING MATERIALS | | | | |
| Opadry Purple YS-1-4845 | Film Coating agent | 3.00 | 17.46 | 272.4@ |
| Purified Water | Vehicle | q.s | q.s# | q.s.# |
| Total weight (3% w/w film Coated tablet) | | NA | 599.46 | 7193.52$ |

@30% extra dispensed to compensate the process loss
Quantity sufficient to prepare 10% w/w of Opadry Purple YS-1-4845 coating solution.
$Quantity includes total weight of uncoated tablets and 3% w/w of coating material.

The weighed quantity of PH100, microcrystalline cellulose (AVICEL PH101), lactose monohydrate (PHARMATOSE 200M), croscarmellose sodium (AC-DI-SOL), hydroxypropyl methylcellulose (HPMC E5) and colloidal silicon dioxide (AEROSIL 200) were manually mixed in a polybag for 5 min before being sifted using a vibratory sifter having an ASTM #40 screen. The magnesium stearate was manually sifted through an ASTM #60 screen. The sifted intragranular materials were blended in a 20 L Conta blender for 10 minutes at 20 rpm. Magnesium stearate then was added for lubrication and the mixture was further blended for 5 minutes at 20 rpm. The lubricated blend was processed in a roller compactor (Settings: Screw feeder 50 rpm, Roller unit 4.0 rpm, Pre Granulator Speed 77.6 rpm, Fine Granulator Speed 100.0 rpm, Hydraulic 75 bar, Roll Gap 3.0 mm for 2 or more cycles until the fines which pass through a #60 screen were ≤25%. The compacted material was blended in a 20 L Conta blender for 5 minutes at 20 rpm. A sample was taken for in-process testing (bulk and tap density, particle size distribution).

The weighed quantity of microcrystalline cellulose (AVICEL PH 200-LM), croscarmellose sodium (AC-DI-SOL) and colloidal silicon dioxide (AEROSIL 200) was manually mixed in a polybag for 5 minutes and then manually sifted through an ASTM #40 screen. The magnesium stearate was manually sifted through an ASTM #60 screen. The roller compacted intragranular blend was added to the blender followed by the extragranular excipients. The materials were blended for 10 minutes at 20 rpm and then the final magnesium stearate was added for lubrication and the final mixture blended for an additional 5 minutes at 20 rpm. Blend homogeneity samples were taken from the top, middle, and bottom. A composite sample was pulled for loss on drying, bulk and tapped density, particle size, and blend flow properties.

Tablets were pressed using a 16.51×0.6.96 mm oval capsule shaped mold. The tablet press was set to achieve the finalized tablet parameters shown in Table 4 below (Compression Machine: Korsch XL100; No. of Punch: double; 20 RPM). Periodic samples were checked by manufacturing for tablet weight, tablet dimensions, tablet hardness, disintegration, and friability throughout the process. The tablets were dedusted and packed into a container with a double lined poly bags.

TABLE 4

| Parameter | Target Value | Range of Parameters |
| --- | --- | --- |
| Average wt. of 20 tablets (mg) | 582.00 | ±5% of target value |
| Individual Tablet weight (mg) | 582.00 | ±5% of target value |
| Friability (300 Rotation) | ≤1.0% | NMT 1.0% |

Tablets were coated with 3% Opadry Purple YS-1-4845 and dried. The tablets were packaged into HPDE bottles. Desiccant was added to protect the tablets.

Example 4: Disintegration

Tablets prepared in Example 3 were placed in a dissolution apparatus in 37° C. water and stirred. The time required for each tablet to disintegrate completely as described in USP <2040> was recorded. Disintegration is defined as that state in which any residue of the unit, except fragments of insoluble coating or capsule shell remaining on the screen of the test apparatus, is a soft mass having no palpably firm core. The disintegration time was determined to be around 8 minutes.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A solid pharmaceutical composition comprising:
    a) an intragranular portion comprising an extract of brown algae which includes more than about 20 wt. % phlorotannin, disintegrant, filler and binder;
    b) an extragranular portion comprising disintegrant, filler, lubricant and binder; and
    c) a coating.

2. The solid pharmaceutical composition of claim 1, wherein the composition is formed into a tablet.

3. The solid pharmaceutical composition of claim 1, wherein the
    composition disintegrates in about 30 minutes or less, about 20 minutes or less, about 15 minutes or less, about 10 minutes or less, about 5 minutes or less or about 3 minutes or less.

4. The solid pharmaceutical composition of claim 1, wherein the composition is an immediate release composition.

5. The solid pharmaceutical composition of claim 2, wherein the tablet has a friability of less than about 1%, less than about 0.8%, less than about 0.5% or less than about 0.3%.

6. The solid pharmaceutical composition of claim 2, wherein the tablet has a hardness of between about 8 Kp and about 25 Kp.

7. The solid pharmaceutical composition of claim 1, wherein the intragranular portion and extragranular portion are present in a ratio (w:w) of between about 3:1 and about 1:1 or of between about 2.15:1 and about 1.95:1.

8. The solid pharmaceutical composition of claim 1, wherein the intragranular portion comprises between about 30% to about 70% extract, between about 20% to about 60% filler, between about 0.5% to about 5% binder and between about 4% to about 11% disintegrant.

9. The solid pharmaceutical composition of claim 1, wherein the intragranular portion further comprises a lubricant and glidant.

10. The solid pharmaceutical composition of claim 9, wherein the intragranular portion comprises between about 30% to about 70% extract, between about 20% to about 60% filler, between about 0.5% to about 5% binder, between about 0.4% to about 1.2% lubricant, between about 0.4% to about 1.2% glidant and between about 6% to about 9% disintegrant.

11. The solid pharmaceutical composition of claim 9, wherein intragranular portion comprises between about 40% to about 60% extract, between about 30% to about 50% filler, between about 0.75% to about 2.5% binder, between about 0.6% to about 1.2% lubricant, between about 0.6% to about 1.2% glidant and between about 4% to about 11% disintegrant.

12. The solid pharmaceutical composition of claim 1, wherein the intragranular portion is compressed to form granules.

13. The solid pharmaceutical composition of claim 1, wherein the extragranular portion comprises between about 70% and about 95% filler and between about 5% and about 30% disintegrant.

14. The solid pharmaceutical composition of claim 1, wherein the extragranular portion further comprises a lubricant and a glidant.

15. The solid pharmaceutical composition of claim 14, wherein the extragranular portion comprises between about 70% and about 95% filler, 5% to 30% disintegrant, 0.5% to 4% lubricant and 0.5% to 4% glidant.

16. The solid pharmaceutical composition of claim 14, wherein the extragranular portion comprises 80% to 90% filler, 7% to 14% disintegrant, 1% to 2% lubricant, and 1% to 2% glidant.

17. The solid pharmaceutical composition of claim 1, wherein the disintegrant is a super disintegrant.

18. The solid pharmaceutical composition of claim 17, wherein the super disintegrant is croscarmellose, cross linked poly vinyl pyrrolidine, crospovidone, sodium starch glycolate, hydroxypropyl cellulose LH-11, hydroxypropyl cellulose LH-21 or combinations thereof.

19. The solid pharmaceutical composition of claim 1, wherein the extract of brown algae is from *Ecklonia cava, Ecklonia kurome, Ecklonia stoloifera, Ecklonia maxima, Ecklonia radiate, Ecklonia bicyclis* and *Ecklonia arborea, Eisenia bicyclis, Eisenia arboraea* or combinations thereof.

20. The solid pharmaceutical composition of claim 1, wherein the extract of brown algae includes about 90 wt. % phlorotannins.

21. The solid pharmaceutical composition of claim 1, further comprising a coating of opaque lavender.

22. The solid pharmaceutical composition of claim 20, wherein the brown algae extract is from *Ecklonia cava*.

* * * * *